(12) United States Patent
Cheng et al.

(10) Patent No.: US 10,028,844 B2
(45) Date of Patent: Jul. 24, 2018

(54) HYDRAULIC ANKLE JOINT

(71) Applicant: KEN DALL ENTERPRISE CO., LTD., New Taipei (TW)

(72) Inventors: Chia-Pao Cheng, New Taipei (TW); Fu-Kuo Wu, New Taipei (TW); Hsiang-Ming Wu, New Taipei (TW)

(73) Assignee: KEN DALL ENTERPRISE CO., LTD., New Taipei (TW)

( * ) Notice: Subject to any disclaimer, the term of this patent is extended or adjusted under 35 U.S.C. 154(b) by 93 days.

(21) Appl. No.: 15/391,785

(22) Filed: Dec. 27, 2016

(65) Prior Publication Data

US 2018/0177615 A1   Jun. 28, 2018

(51) Int. Cl.
  *A61F 2/50* (2006.01)
  *A61F 2/66* (2006.01)
  *A61F 2/74* (2006.01)

(52) U.S. Cl.
  CPC .... *A61F 2/6607* (2013.01); *A61F 2002/5038* (2013.01); *A61F 2002/745* (2013.01)

(58) Field of Classification Search
  CPC .... A61F 2/64; A61F 2/644; A61F 2/66; A61F 2/6607; A61F 2002/74; A61F 2002/744; A61F 2002/745
  See application file for complete search history.

(56) References Cited

U.S. PATENT DOCUMENTS

| 5,957,981 A * | 9/1999 | Gramnas | A61F 2/6607 |
| | | | 623/47 |
| 8,206,458 B1 * | 6/2012 | Hawkins | A61F 2/6607 |
| | | | 623/26 |
| 2014/0371874 A1 * | 12/2014 | Wu | A61F 2/80 |
| | | | 623/47 |

* cited by examiner

*Primary Examiner* — Thomas J Sweet
*Assistant Examiner* — Christie Bahena
(74) *Attorney, Agent, or Firm* — Leong C. Lei

(57) ABSTRACT

The hydraulic ankle joint includes a main member having a fluid supply chamber storing a hydraulic fluid, a first pressure regulating chamber, a second pressure regulating chamber, and a space connecting the chambers. The space houses an axle element rotatably joined to the main member. The main member is rotatably mounted on a U-shaped hinge seat. An extension piece is extended radially from the circumference of the axle element. A fluid block penetrates through the main member and into the space. The extension piece and the fluid block jointly partition the space into a front chamber and a back chamber. The first and second pressure regulating chambers adjust the back and front chambers' pressure so that impact from walking may be effectively buffered. The fluid supply chamber automatically refills hydraulic fluid into the front and back chambers so as to reduce user maintenance overhead.

5 Claims, 7 Drawing Sheets

HYDRAULIC ANKLE JOINT

BACKGROUND OF THE INVENTION

(a) Technical Field of the Invention

The present invention is generally related to prosthetic ankle joint, and more particular to a hydraulic ankle joint capable of buffering the impact from walking.

(b) Description of the Prior Art

Prosthetic joints have evolved from employing cushion materials to those integrating pneumatic and hydraulic mechanisms, so as to improve impact absorption and walking in a more natural manner.

Conventional prosthetic joints usually rely on multiple connection mechanisms to simulate the operation of healthy joints. They often do provide certain flexible and buffering capability, but the impact from walking and other activities cannot be completely eliminated, and the walking style is rather rigid.

US Pre-grant publication No. 2014/0074255 teaches an artificial ankle includes a housing containing a hollow body, a vane type piston arranged in the hollow body, and a gravity controlled means. A hydraulic fluid is stored within the hollow body. The van type piston partitions the hollow body into a front chamber and a back chamber. The van type piston has a channel connecting the two chambers. The channel is configured with a magnetic valve which will be tilted for different angles as a user of the ankle joint walks. A magnetic element on the magnetic valve, therefore, moves to open or close the magnetic valve so as to balance the pressure of the hydraulic fluid in the two chambers, and thereby further lessen the impact from walking.

However, the artificial ankle joint is rather complicated, and therefore maintenance and repair is not convenient. Within a magnetic environment, whether the magnetic valve would be interfered would pose a safety concern. In addition, if there is not enough hydraulic fluid, the user has refill the hydraulic fluid by himself/herself, which is quite inconvenient.

SUMMARY OF THE INVENTION

Therefore, a novel hydraulic ankle joint is provided, which includes a main member having a fluid supply chamber storing a hydraulic fluid, a first pressure regulating chamber, a second pressure regulating chamber, and a space connecting the chambers. The space houses an axle element rotatably joined to the main member. The main member is rotatably mounted on a U-shaped hinge seat. An extension piece is extended radially from the circumference of the axle element. A fluid block penetrates through the main member and into the space. The extension piece and the fluid block jointly partition the space into a front chamber and a back chamber.

During walking, the extension piece turns along with the axle element so as to adjust the pressure in the front and back chambers. The first and second pressure regulating chambers further balance the back and front chambers' pressure so that impact from walking may be effectively buffered and the walking style is more natural. The fluid supply chamber automatically refills hydraulic fluid into the front and back chambers so as to reduce user maintenance overhead.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
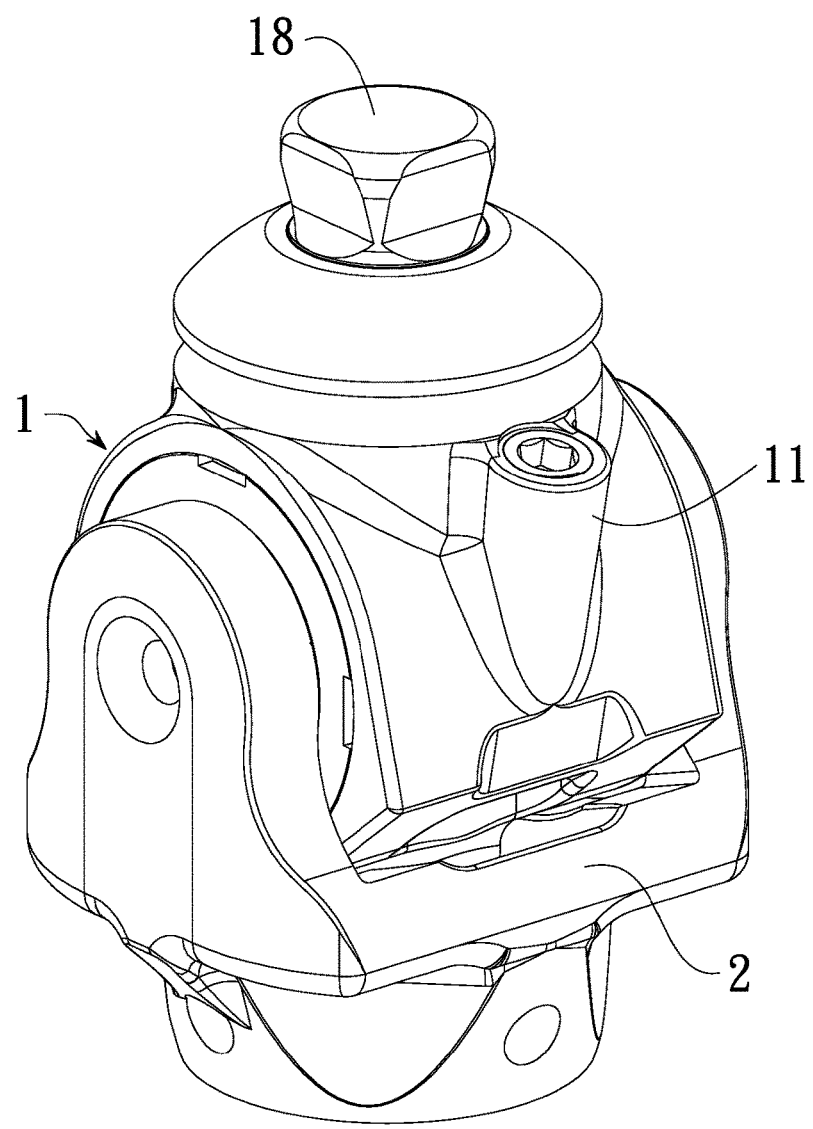
FIG. 1 is a perspective diagram showing a hydraulic ankle joint according to an embodiment of the present invention.
Figure 2:
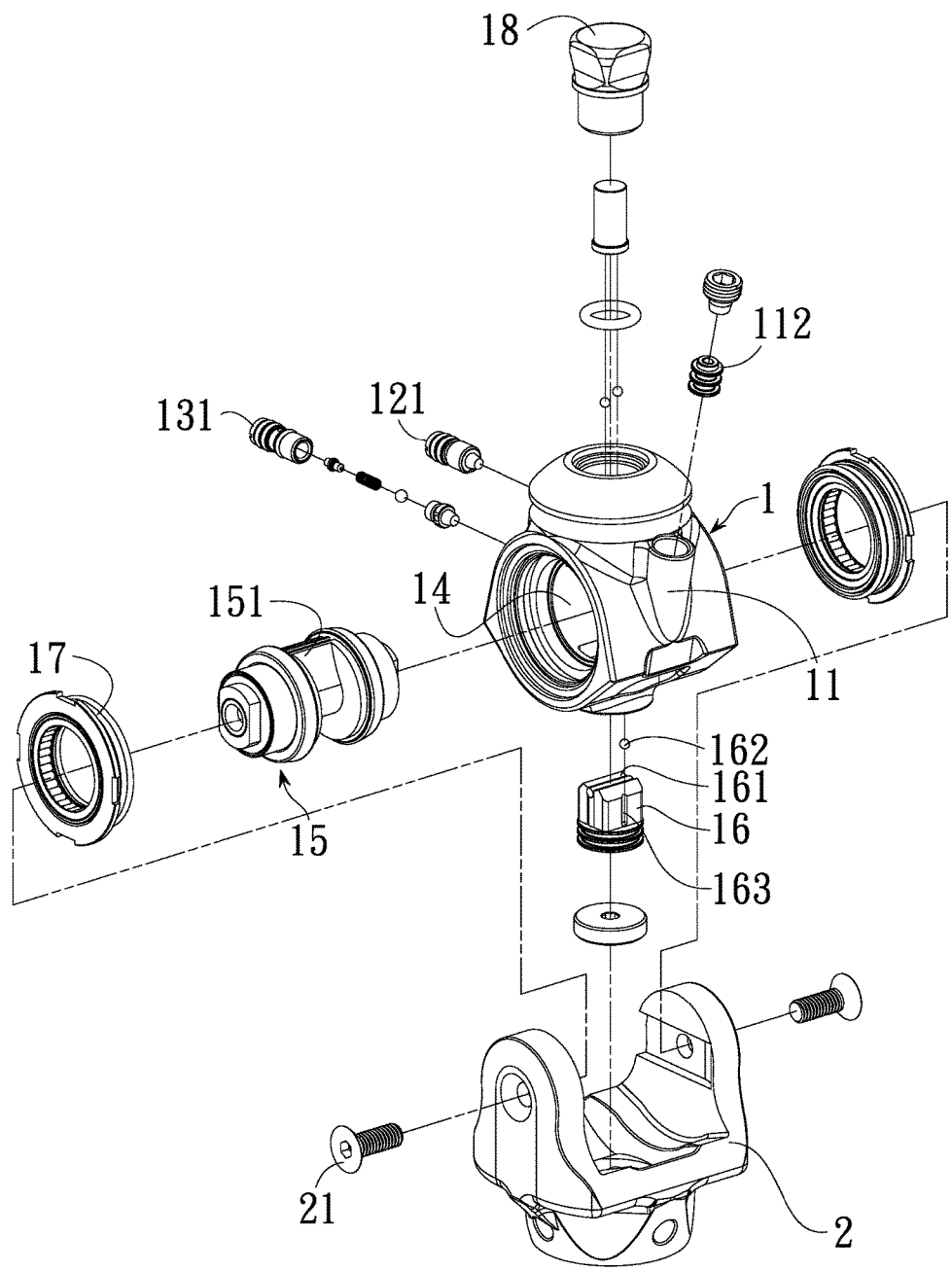
FIG. 2 is a perspective break-down diagram showing the hydraulic ankle joint of FIG. 1.
Figure 3:
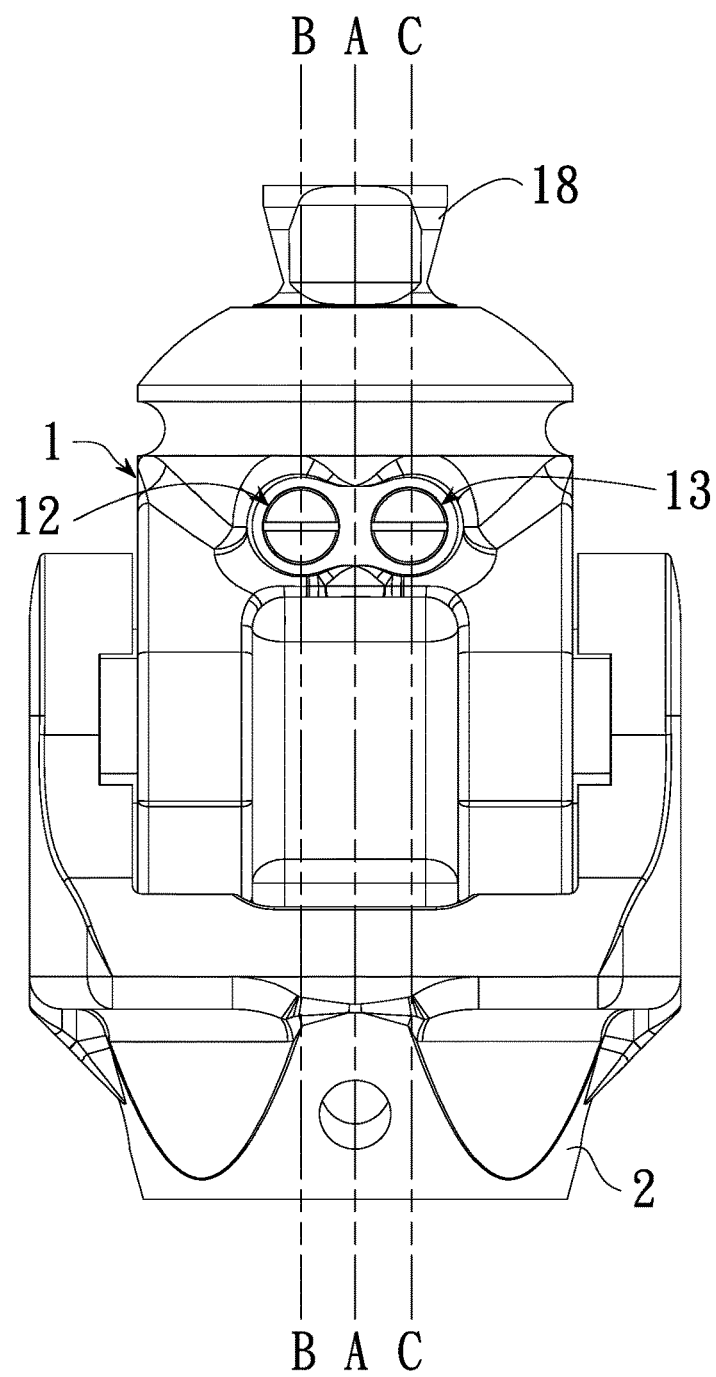
FIG. 3 is a schematic rear-view diagram showing the hydraulic ankle joint of FIG. 1 and three cross-sectional lines: A-A, B-B, and C-C.

As shown in FIGS. 1 to 7, a hydraulic ankle joint according to an embodiment of the present invention includes a main member 1 having a connection seat 18 on a top side, and a hinge seat 2 rotatably joined to a bottom side of the main member 1. A prosthetic leg is joined to the connection seat 18, and a prosthetic foot is joined to a hinge seat 2. The main member 1 includes a fluid supply chamber 11, a first pressure regulating chamber 12, a second pressure regulating chamber 13, and a space 14 connecting the chambers 11, 12, 13, all housed inside the main member 1. The fluid supply chamber 11 is configured to a first side, and the first and second pressure regulating chambers 12 and 13 are configured to a second opposite to the first side of the main member 1. As shown in FIG. 3, the chambers 11, 12, 13 are independent and non-interfering with each other. The first pressure regulating chamber 12 functions when the heel of the prosthetic foot touches the ground, and the second pressure regulating chamber 13 functions when a handicapped equipped with the hydraulic ankle joint walks forward. An axle element 15 runs laterally through the space 14 whose two ends are rotatably joined to the main member 1 through two positioning elements 17, respectively. The main member 1 including the axle element 15 is rotatably mounted between the U-shaped hinge seat 2's two upwardly extending arms by fastening a locking bolt 21 into a hole at each end of the axle element 15 through one of the arms. The main member 1, therefore, may swing relative to the hinge seat 2.

As shown in FIGS. 1 to 6, an extension piece 151 is configured axially in a middle section of the axle element 15 and extended radially from the circumference of the axle element 15. The main member 1 has a bottom opening so as to allow a fluid block 16 to penetrate through and into the space 14. The fluid block 16 has a blocking rubber 161 along a top edge that tightly contacts the axle element 15. When the axle element 15 is placed in the space 14, the extension piece 151 and the fluid block 16 jointly partition the space 14 into a front chamber 4 and a back chamber 5. The front and back chambers 4 and 5 are connected to a first channel 122 and a second channel 132. As the axle element 15 turns, the channels 122 and 132 allow fluid to flow between the chambers 4 and 5 so as to balance their pressures. The fluid is preferably a lubricating oil but is not limited as such.

Figure 4:
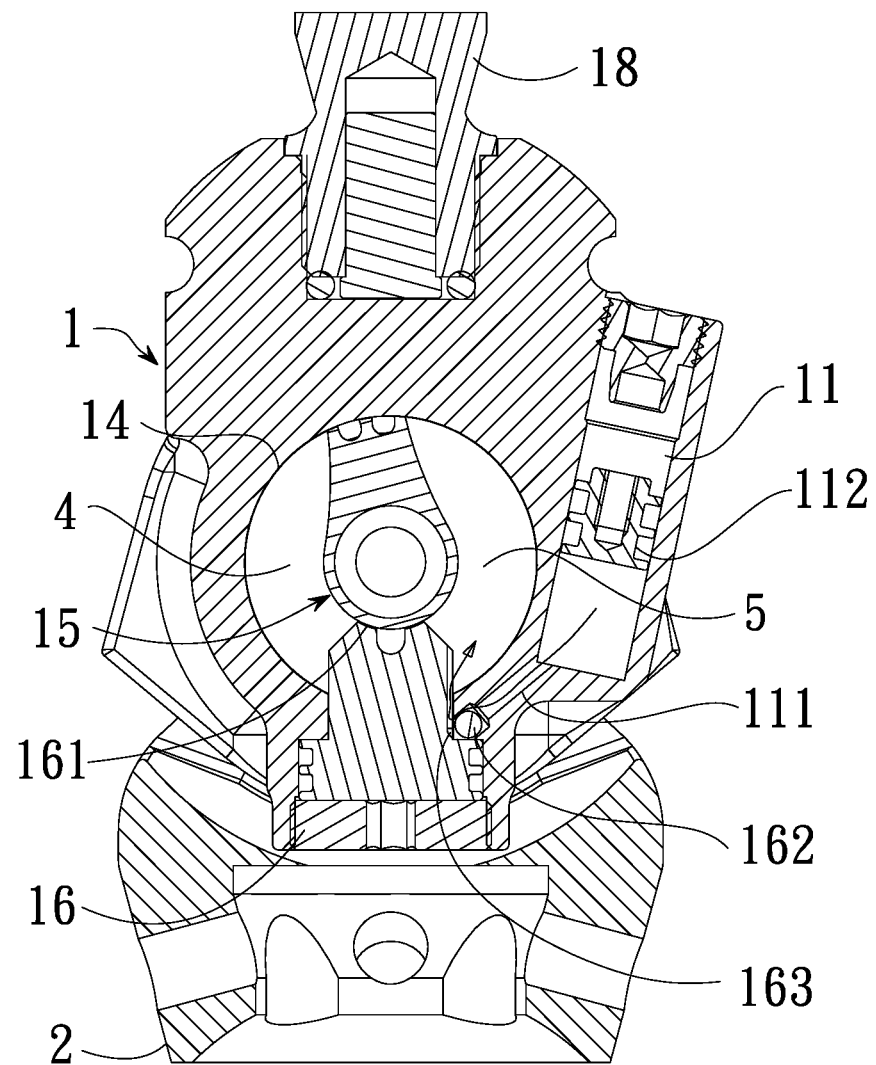
FIG. 4 is a schematic cross-sectional diagram along a A-A line of FIG. 3 showing the supply of a hydraulic fluid through a fluid supply tunnel.

As shown in FIG. 4, which is a cross-sectional diagram along the A-A line of FIG. 3, the fluid supply chamber 11 has a supply piston 112 inside and a supply tunnel 111 connecting a bottom side of the fluid supply chamber 11 and the space 14. A ditch 163 is configured on a side of the fluid block 16, and a ball 162 is movably housed in the ditch 163. When the fluid in the back chamber 5 is less than a certain amount, the supply piston 112 would drive fluid through the supply tunnel 111 to push the ball 162 downward, and then into the back chamber 5. Until there is enough fluid in the back chamber 5, the ball 5 would rise to block the supply tunnel 111 under pressure. As such, the fluid is automatically refilled and user manual refill is avoid. However, after extended period of usage, the fluid in the fluid supply chamber 11 still has to be refilled manually.

Figure 5:
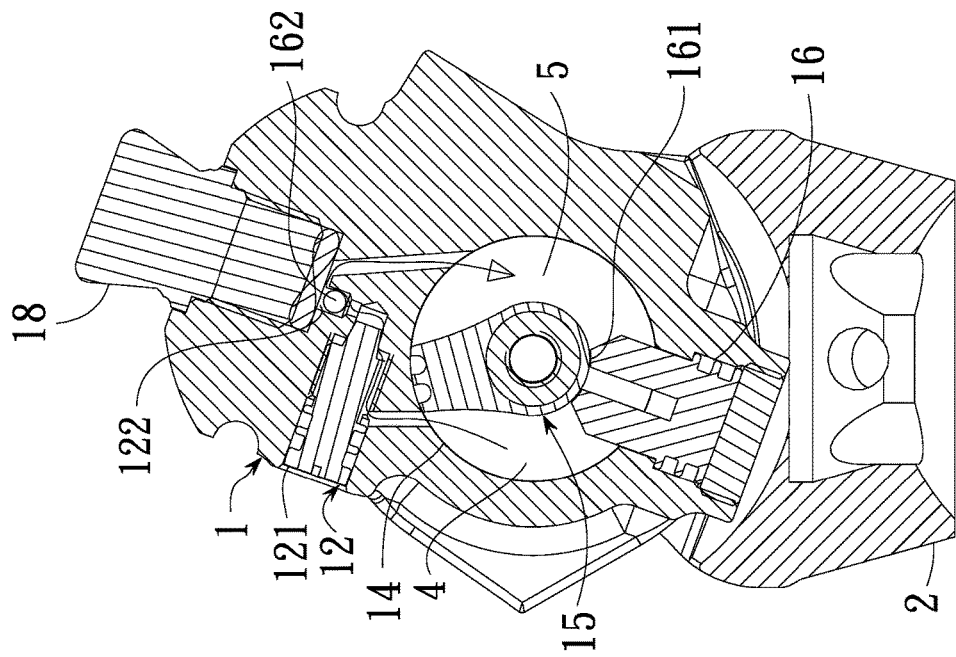
FIG. 5 is a schematic cross-sectional diagram along a B-B line of FIG. 3 showing a hydraulic fluid flow path through a first channel.
Figure 5:
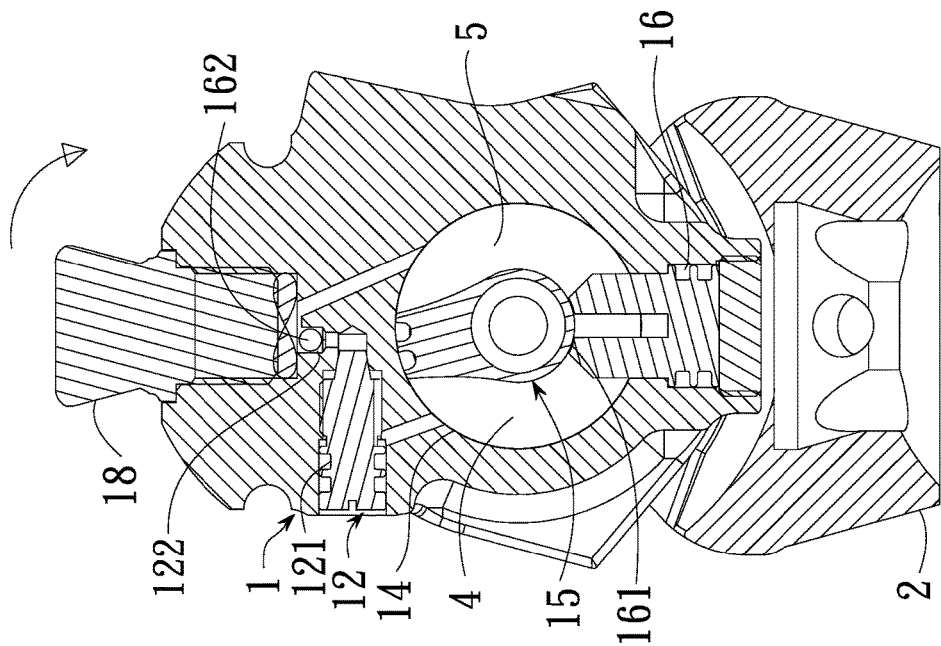
Figure 6:
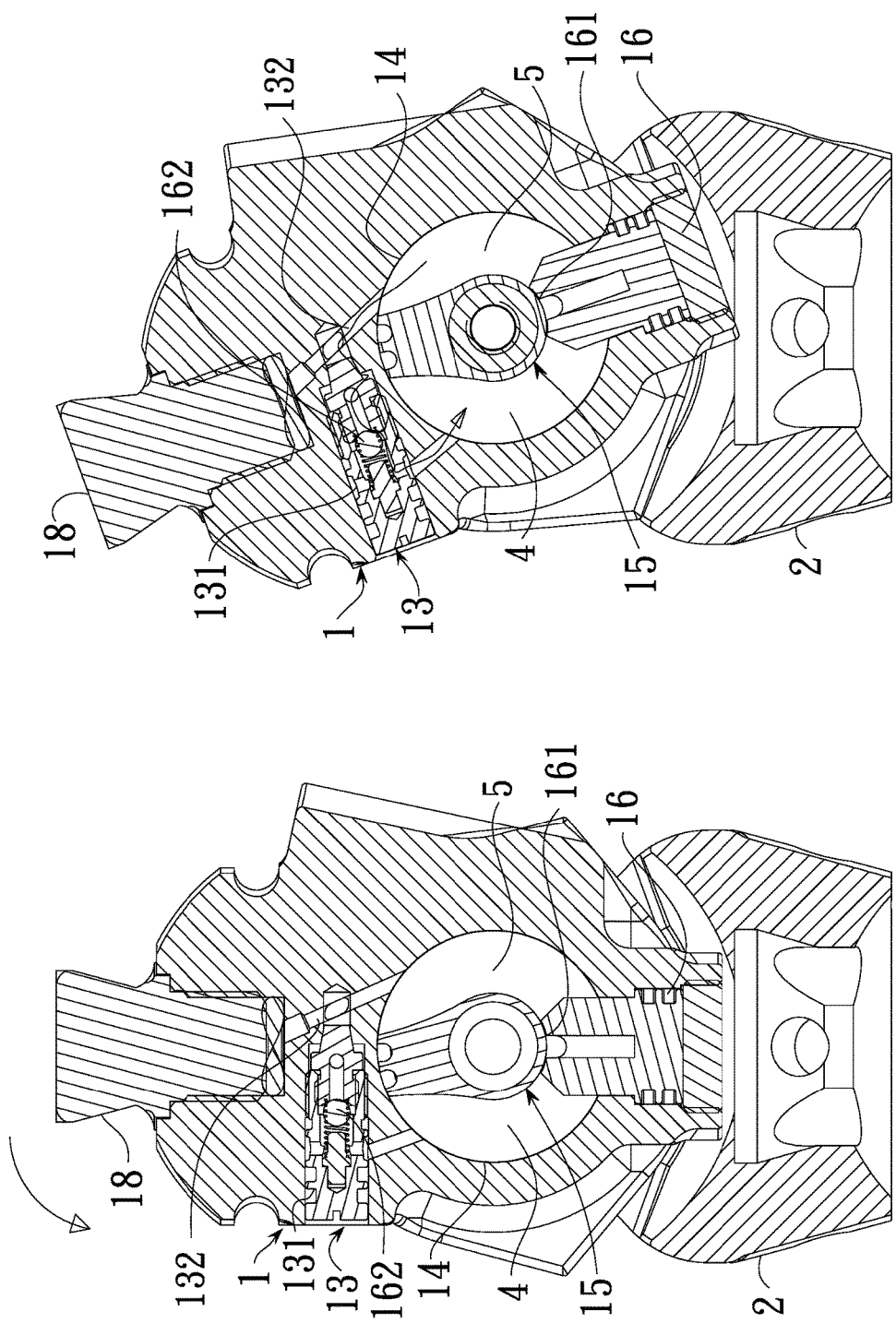
FIG. 6 is a schematic cross-sectional diagram along a C-C line of FIG. 3 showing a hydraulic fluid flow path through a second channel.

The first pressure regulating chamber 12 corresponds to the first channel 122, and a first knob 121 adjusts the pressure of the first channel 122. As shown in FIG. 5, which is a cross-sectional diagram along the B-B line of FIG. 3, when the main member 1 tilts backward, the fluid in the front chamber 4 is pressurized to push a ball 162 in the first channel 122 upward. Fluid, therefore, flows through the first channel 122 into the back chamber 5 so that the fluid in the chambers 4 and 5 are balanced pressure-wise. After the pressure is balanced, the ball 162 would be driven downward to block the first channel 122. Similarly, the second pressure regulating chamber 13 corresponds to the second channel 132, and a second knob 131 adjusts the pressure of the second channel 132. As shown in FIG. 6, which is a cross-sectional diagram along the C-C line of FIG. 3, when the main member 1 tilts forward, the fluid in the back chamber 5 is pressurized to push a ball 162 in the second channel 132. Fluid, therefore, flows through the second channel 132 into the front chamber 4 so that the fluid in the chambers 4 and 5 are balanced pressure-wise. After the pressure is balanced, the ball 162 would be restored to block the second channel 132. The first and second knobs 121 and 131 are configured with a specially formed shape such as a slotted shape that allows them to be turned, or driven, with a tool.

Figure 7:
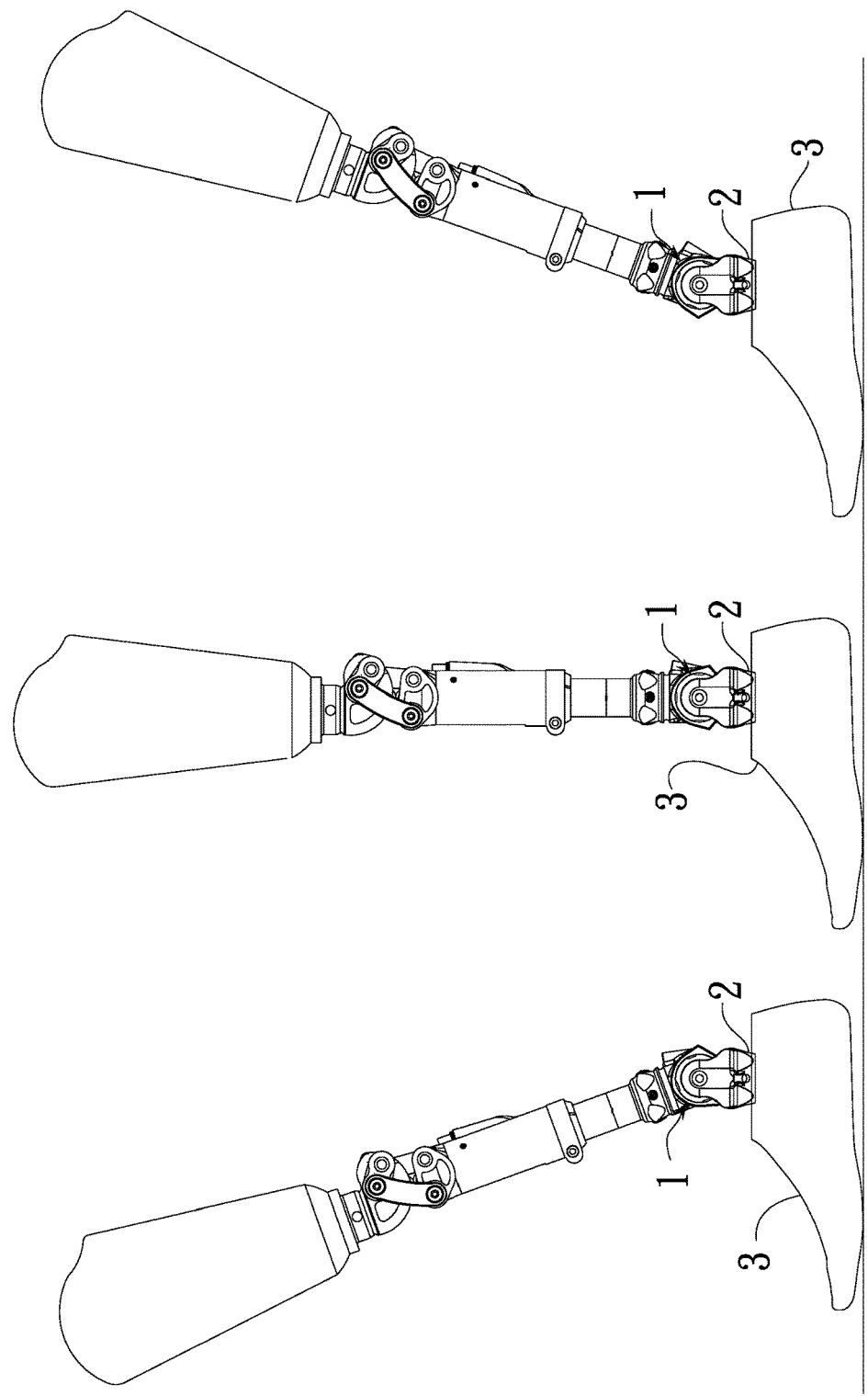
FIG. 7 is a schematic diagram showing a scenario of the hydraulic ankle joint during walking.

FIG. 7 provides a scenario of the hydraulic ankle joint during walking. As shown, the prosthetic foot 3 always contacts with the ground flatly. The main chamber 1 periodically tilts forward and backward. Through the pressure difference between the front and back chambers 4 and 5, the hydraulic fluid would flow between them, so as to reduce the impact from the ground and make the walking style more natural.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the claims of the present invention.

We claim:
1. A hydraulic ankle joint, comprising
a U-shaped hinge seat;
a main member having a fluid supply chamber storing a hydraulic fluid, a first pressure regulating chamber, a second pressure regulating chamber, and a space connecting the chambers, all housed inside the main member; and
an axle element running laterally through the space whose two ends are rotatably joined to the main member through two positioning elements, respectively; wherein
the main member together with the axle element is rotatably mounted between the U-shaped hinge seat's two upwardly extending arms by fastening a locking bolt into each end of the axle element through one of the arms;
an extension piece is configured axially in a middle section of the axle element and extended radially from the circumference of the axle element; the main member has a bottom opening so as to allow a fluid block to penetrate through and into the space; the extension piece and the fluid block jointly partition the space into a front chamber and a back chamber;
the first pressure regulating chamber adjusts the back chamber's pressure; the a second pressure regulating chamber adjusts the front chamber's pressure; the fluid supply chamber automatically refills hydraulic fluid into the front and back chambers consumed by the hydraulic ankle joint's activity.

2. The hydraulic ankle joint according to claim 1, wherein the first pressure regulating chamber comprises a first knob and a first channel; the first channel is inside the main member above and connecting the space for, when the main member tilts backward, guiding the fluid in the front chamber to flow into the back chamber so that the fluid in the chambers are balanced pressure-wise, and the first knob adjusts the pressure of the first channel.

3. The hydraulic ankle joint according to claim 1, wherein the second pressure regulating chamber comprises a second knob and a second channel; the second channel is inside the main member above and connecting the space for, when the main member tilts forward, guiding the fluid in the back chamber to flow into the front chamber so that the fluid in the chambers are balanced pressure-wise, and the second knob adjusts the pressure of the second channel.

4. The hydraulic ankle joint according to claim 1, wherein the fluid supply chamber has a supply piston inside and a supply tunnel connecting a bottom side of the fluid supply chamber and the space for automatically refilling hydraulic fluid into the space.

5. The hydraulic ankle joint according to claim 1, wherein the fluid block has a blocking rubber along a top edge that tightly contacts the axle element; and, as the axle element turns, the extension piece adjusts the hydraulic fluid in the front and back chambers.

\* \* \* \* \*